(12) United States Patent
Bisschops et al.

(10) Patent No.: US 7,619,102 B2
(45) Date of Patent: Nov. 17, 2009

(54) PURIFICATION OF MUPIROCIN

(75) Inventors: Marc Antonius Theodorus Bisschops, Breda (NL); Tiemen Geert Pieter Reijns, The Hague (NL); Anita Mathiesen, Stabekk (NO); Lene Aassveen, Oslo (NO)

(73) Assignee: Axellia Pharmaceuticals ApS (DK)

( * ) Notice: Subject to any disclaimer, the term of this patent is extended or adjusted under 35 U.S.C. 154(b) by 0 days.

(21) Appl. No.: 11/816,439

(22) PCT Filed: Feb. 21, 2006

(86) PCT No.: PCT/EP2006/001672

§ 371 (c)(1),
(2), (4) Date: Mar. 24, 2008

(87) PCT Pub. No.: WO2006/087237

PCT Pub. Date: Aug. 24, 2006

(65) Prior Publication Data

US 2008/0234503 A1 Sep. 25, 2008

(30) Foreign Application Priority Data

Feb. 21, 2005 (DK) ................................ 2005 00261

(51) Int. Cl.
*C07D 407/06* (2006.01)

(52) U.S. Cl. ...................................... 549/414; 549/554

(58) Field of Classification Search ................. 549/414, 549/554; 514/460
See application file for complete search history.

(56) References Cited

U.S. PATENT DOCUMENTS

| | | | |
|---|---|---|---|
| 3,977,943 A | 8/1976 | Barrow et al. | |
| 4,071,536 A | 1/1978 | Barrow et al. | |
| 4,222,942 A | 9/1980 | O'Hanlon et al. | |
| 4,289,703 A | 9/1981 | Barrow et al. | |
| 5,569,672 A | 10/1996 | Baker et al. | |
| 5,594,026 A | 1/1997 | Greenway et al. | |

FOREIGN PATENT DOCUMENTS

| | | |
|---|---|---|
| WO | 0046388 | 8/2000 |
| WO | 0046389 | 8/2000 |

OTHER PUBLICATIONS

Kirk-Othmer "Encyclopeida of Chem. Tech." p. 95-147 (2002).*
International Search Report; International Application No. PCT/EP2006/001672; International Filing Date Feb. 21, 2006; Applicant's File Reference APWO06889; Date of Mailing Jul. 17, 2006; 5 pages.
Written Opinion of International Searching Authority; International Application No. PCT/EP2006/001672; International Filing Date Feb. 21, 2006; Applicant's File Reference APWO06889; Date of Mailing Jul. 17, 2006; 6 pages.

* cited by examiner

*Primary Examiner*—Bernard Dentz
*Assistant Examiner*—David E Gallis
(74) *Attorney, Agent, or Firm*—Cantor Colburn LLP

(57) ABSTRACT

A method for purification of the antibiotic mupirocin (pseudomonic acid A) which comprises: a) Causing or allowing precipitation of mupirocin from an aqueous solution thereof; b) Recovering the precipitate; c) Dissolving the recovered precipitate in an organic solvent.

15 Claims, No Drawings

PURIFICATION OF MUPIROCIN

FIELD OF INVENTION

The present invention relates to a method for purification of the antibiotic mupirocin (pseudomonic acid A).

BACKGROUND OF INVENTION

It is known that *Pseudomonas fluorescens* strains are able to biosynthesize, in addition to pseudomonic acid A, other related antibiotics designated by the letters B-D in small quantities [E. B. Chain, G. Mellows, *J. Chem. Soc. Perkin Trans I.* 318 (1977); J. P. Clayton et al., *Tetrahedron Lett.*, 21, 881 (1980); P. J. O. Hanlon, N. H. Rogers, *J. Chem. Soc. Perkin Trans I.* 2665 (1983)]. Among the pseudomonic acid antibiotics, from a therapeutic point of view the most valuable is pseudomonic acid A, which has a growth inhibiting effect mainly against Gram positive bacteria.

One method for the isolation of pseudomonic acid A from the antibiotic complex-containing culture broth is the liquid-liquid extraction. According to German Patent No. 2227739 and U.S. Pat. No. 4,289,703, soluble barium salts are added to the fermentation broth, then the microorganism cells with the insoluble inactive agents are separated by centrifugation and finally the antibiotics are extracted by methyl isobutyl ketone (MIBK). The antibiotics are then removed from the methyl isobutyl ketone extract by alkaline water and the resulting alkaline aqueous extract is cleaned by reextraction with methyl isobutyl ketone. The crude product obtained is chromatographed, and an ester derivative is prepared from the pseudomonic acid antibiotic complex and purified with preparative thin layer chromatography. The acid form of the pure antibiotic is obtained by hydrolysis.

Belgian Patent No. 870,855 relates to a process in which the culture broth is extracted with methyl isobutyl ketone and from the extract the active substance is extracted by sodium hydrogen carbonate solution. Materials insoluble in alkaline water are separated by filtration, then the pH of the filtrate is acidified and extracted by methyl isobutyl ketone. Finally the pseudomonic acid A is obtained by the concentration of the extract and crystallization from a methyl isobutyl ketone-n-heptane mixture.

U.S. Pat. No. 4,222,942 relates to a process for the isolation of mupirocin by extracting a solution of crude mupirocin preparation in a water immiscible organic solvent with an aqueous media, lowering the pH of said aqueous solution, and extracting the solution with a polar water immiscible organic solvent and thereafter adding a diluent which is sufficiently non-polar to reduce the polarity of, but is miscible with, said polar organic solvent so as to effect crystallization of mupirocin. The steps of this reaction scheme are manifold and, as a consequence, the scheme requires a large quantity of solvent.

U.S. Pat. No. 6,254,921 discloses a process for the isolation of mupirocin comprising extracting an acidified culture broth using a chlorinated aliphatic hydrocarbon or isobutyl acetate, such that a mupirocin-containing extract is obtained; and purifying the mupirocin from said extract by distributing the extract between an aqueous phase and an organic phase comprising at least one organic solvent and evaporating the organic solvent.

None of the above methods are satisfactory from a commercial and ecological view. Accordingly, there remains a need for a novel method for purification of mupirocin, which is free from at least some of the disadvantages of the known processes and the application of which, in production scale, may result in a high yield of the recovery of the above-mentioned antibiotic.

The present invention provides a method for purification of mupirocin, which meets at least some of the above defined objectives in that it is economically sound and, preferably, less ecologically deleterious, and results in a high yield of mupirocin having a high purity. The method comprises precipitation of mupirocin from an aqueous solution of mupirocin, and dissolution of the precipitate in an organic solvent.

The present invention relates to a method for purifying mupirocin, comprising the steps of:
 a) precipitation of mupirocin from an aqueous solution of mupirocin;
 b) recovery of the precipitate;
 c) dissolution of the precipitate in an organic solvent; and optionally
 ci) recovery of mupirocin from the solvent.

The term "mupirocin" is meant to comprise mupirocin as defined in any of the above-mentioned references, as well as natural occurring and synthetic derivatives thereof. The term comprises the acidic form and salts thereof, such as the calcium salt, as well as solvates and polymorphic forms of these.

In an embodiment of the invention, the solution of mupirocin is fermentation broth, such as clarified broth, such as clarified by centrifugation or filtration. The source of the fermentation broth is not crucial, and the broth can be obtained as disclosed in the prior art, for example as disclosed in the above-mentioned references, in U.S. Pat. Nos. 3,977,943, 4,071,536 and 4,289,703, WO 00/46389 or WO 03/000910. Optionally, the broth can be concentrated before precipitation of mupirocin. Solutions other than fermentation broths can be used, e.g. a solution resulting from chemical synthesis of mupirocin or a derivative thereof.

Mupirocin may be precipitated from the aqueous solution by adding an acid, such as an acid selected from the group consisting of acetic acid; citric acid; sulfuric acid; and hydrochloric acid. When using an acid, the pH during precipitation conveniently is in the range of 2.0 to 6.0, preferably in the range of 3.5 to 5.0, and most preferred in the range of 4.2 to 4.6. In one embodiment the solution is left stirring until mupirocin has precipitated, such as for a period of 10-40 minutes.

The mupirocin containing precipitate may be recovered by centrifugation or filtration, centrifugation being preferred. The centrifugation should be carried out under such conditions that a gel is formed, e.g. by centrifuging for 5-30 minutes at 5000-15000 g, or in an continuous centrifuge at 5000-15000 g.

In an embodiment of the invention, the recovered precipitate is dissolved in a polar, substantially water immiscible organic solvent. As solvent, a ketone, e.g. having the formula alkyl-C(=O)-alkyl, such as methyl isobutyl ketone; an ester, e.g. having the formula alkyl-C(=O)—O-alkyl, such as ethyl acetate; an alkanol, e.g. having the formula alkyl-OH, such as n-butanol; or a mixture comprising any of these can be used. Herein, the term "alkyl" when referring to alcohols, refers to aliphatic hydrocarbon groups of greater than four carbons and includes a straight or branched chain aliphatic hydrocarbon group that is saturated or unsaturated and, in other solvents, the term "alkyl" refers to a straight or branched chain aliphatic hydrocarbon group which is saturated or unsaturated and has 1, 2, 3, 4, 5, 6 or more carbon atoms.

Presently it is preferred that the solvent is pure methyl isobutyl ketone (MIBK). That is the solvent should comprise more that 90% (such as more than 92%, more than 94%, more than 96%, or even more than 98% or 99%) MIBK. If needed, the mupirocin can be recovered from the solvent, such as by crystallization, optionally after water removal from the solvent.

In another embodiment, the method of the invention comprises one or more further steps, in order to obtain a more pure antibiotic. Such steps might be applied before step a) and/or after step d), and/or between steps a) and b) and/or between steps b) and c) and/or after step c), and comprises steps selected from the group consisting of: a decolourisation step; a step for removal of hydrophilic components; a concentration step; an evaporation step; a clarification step; a water removal step; a drying step; a filtration step; an extraction step; and a crystallization step. It is presently preferred that the further step(s) are applied after the step d) above.

The method of the invention is preferably carried out at a temperature between the freezing point of the solutions and room temperature, such as a temperature in the range 0-25° C., more preferred in the range 5-20° C. Optionally drying and evaporation steps can be carried out at an elevated temperature, such as in the range 20-50° C.

The invention also relates to mupirocin obtained by a method of the invention. The mupirocin of the invention is more pure than mupirocin obtained by the methods of the prior art. By the method of the invention, it is possible to obtain mupirocin having a purity of at least 93%, for example at least 95%, preferably least 96%, more preferably least 97% and most preferably even at least 98%. Typically, the mupirocin of the invention has a specific activity of at least 950 µg/mg, and preferably at least 960 µg/mg.

Following the teaching of the prior art (e.g. U.S. Pat. Nos. 5,569,672 and 5,594,026, the entire disclosure of which is incorporated by reference herein) it is also possible to generate calcium salts and different polymorphic forms of pseudomonic acid.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All values mentioned herein should be understood as being preceded by "about", i.e. "7" should be understood as "about 7". All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The content of the prior art references are hereby incorporated herein in their entirety by reference.

EXAMPLES

Example 1

Obtaining a Cell Free Solution of Mupirocin in Water

Example 1A

A fermentation broth containing mupirocin was obtained by fermenting a mupirocin producing culture of *Pseudomonas fluorescens* in a manner known per se, i.e. in line with the procedure of Example 1 in U.S. Pat. No. 3,977,943.

2 l mupirocin containing whole culture fermentation broth from a laboratory fermentor was adjusted to pH=7.1 (by addition of 1 M NaOH) and stirred at room temperature for 30 minutes. A cell free solution was obtained by centrifugation for 10 minutes in a laboratory centrifuge at 10,000 g (5° Celsius). About 90% of the mupirocin present in the fermentation broth was recovered in the final clarified solution.

Example 1B 5 l mupirocin fermentation broth obtained as in example 1a was adjusted to pH=8.3 (by addition of 3 M NaOH) and filtered through a 144 µm metal screen at room temperature, followed by ultra-filtration (Millipore Pellicon-2 Biomax-5). About 70% of the mupirocin present in the fermentation broth was recovered in the final clarified solution.

Example 1C 2600 l mupirocin fermentation broth obtained as in Example 1A was adjusted to pH=7.5 (by addition of 20% NaOH) and filtered through a 0.1 µm ceramic filter (SCT/Exekia Membralox P19-40,0.1-α-alu modules). Residual mupirocin was recovered by diafiltration of the biomass in batch mode with 3*500 l water. Subsequently, the mupirocin containing permeate was concentrated by RO (Osmonics Desal DK membrane). It was found that 80% of the mupirocin present in the fermentation broth was recovered in the final clarified solution.

Example 2

Aqueous Precipitation at Low pH

Example 2A 2 l filtrate obtained as in example 1c was transferred into centrifuge bottles and 40 ml concentrated acetic acid was slowly added under stirring. Resulting pH was 4.5. The sample was left stirring at room temperature for 30 minutes before centrifugation in a refrigerated centrifuge at 13,000 g for 20 minutes. The supernatant was poured off leaving a gel, containing 0.6 g mupirocin/g gel. Total recovery in the precipitation was 90%.

Example 2B 1000 l clarified aqueous mupirocin solution obtained as in Example 1c was precipitated by lowering the pH to 4.5. About 50 l 60% acetic acid were mixed in line with the filtrate. The precipitate was collected by an industrial separator (Westfalia CSA-19), yielding a mupirocin gel containing 0.333 g mupirocin/g gel.

Example 2C 600 ml filtrate obtained as in Example 1A was transferred into centrifuge bottles and pH was adjusted to 4.4 by slowly adding 2 ml concentrated hydrochloric acid under stirring. The sample was left stirring at room temperature for 30 minutes before centrifugation in a refrigerated centrifuge at 13,000 g for 20 minutes. The supernatant was poured off leaving a gel.

Example 3

Repeated Aqueous Precipitation at Low pH 3 ml aqueous precipitate obtained as in Example 2a was dissolved in 16 ml of 8% ammonium hydroxide. pH of the resulting clear solution (pH=8.5) was adjusted to 4.4 by addition of 3 ml concentrated acetic acid. The sample was left at 4°Celsius over night before centrifugation in a refrigerated centrifuge at 13,000 g for 20 minutes. The supernatant was poured off leaving a gel. Total recovery in the second precipitation was 99%.

Example 4

Dissolution of Mupirocin in Organic Solvent

Example 4A

Aqueous precipitate containing 25 g of mupirocin obtained as in Example 2a was dissolved in 250 ml of MIBK. The mixture was filtered.

Example 4B

Aqueous precipitate containing 25 g of mupirocin obtained as in Example 2a was dissolved in 250 ml of ethyl acetate. The mixture was filtered.

Example 5

Further Purification

Example 5A

Removal of Hydrophilic Components 180 ml of mupirocin in MIBK obtained as in Example 4a was transferred to a separation funnel and extracted with 20 ml of MilliQ water. The two phases were left to separate and the aqueous phase was removed and discarded. The extraction of the organic phase was repeated 4 times and mupirocin was thereafter recovered from the organic phase.

Example 5B

Color Removal by Carbon Treatment 180 ml of mupirocin in MIBK obtained as in Example 4a was added 4.5 g of activated carbon (Norit C extra) and left stirring for 30 minutes before the carbon was filtered off and the filter cake washed with 30 ml MIBK.

Example 6

Crystallization

Example 6A

Preparation of Pseudomonic Acid Polymorphous Form I 200 ml of the organic solution obtained in Example 5a, containing 17 g mupirocin, was evaporated under vacuum In a laboratory rotary evaporator (60 mbar, 40° C.). The evaporation was stopped when 102 ml solution was left in the product flask. 5 ml heptane was added and the solution was left with stirring at room temperature. After 22 hours with stirring the crystalline material was filtered. The filter cake was washed three times with 40 ml MIBK, and thereafter dried (<50 mbar, 40° C.). 13.2 g dry product was recovered with a specific activity of 960 µg/mg (measured by HPLC).

Example 6B

Preparation of Pseudomonic Acid Polymorphous Form II 100 ml of organic solution, containing 17 g mupirocin, obtained as described in Example 5b, is added 150 ml heptane over about 2 hours with stirring. After about 24 hours with stirring the crystalline material is filtered, washed with MIBK/heptane (50/50) and dried in a vacuum drier (<50 mbar, 40° C.).

Example 6C

Preparation of Polymorphous Form III 100 ml of organic solution, containing 17 g mupirocin, obtained as described in Example 4b, is added 90 ml heptane with stirring. The solution is heated to 40° C., and held at this temperature for the rest of the procedure. The solution is seeded with crystalline product obtained from Example 6A. After three days with stirring the crystalline material is filtered, washed with MIBK/heptane (50/50) and dried in a vacuum drier (<50 mbar, 40° C.).

Example 6D

Preparation of Calcium Pseudomonate

Aqueous precipitate obtained as in Example 2A containing 25 g mupirocin is slowly dissolved with sodium hydroxide solution (1M, 45 ml) to give a neutral solution (pH 7). The solution is filtered. Calcium chloride (6.3 g) is added the mixture and stirring is maintained to give a clear solution. After standing for 20 hours the crystalline product is filtered off, washed with water (50 ml) and dried (50 mbar, 40° C.) to give calcium pseudomonate dihydrate.

Example 6E

Preparation of Calcium Pseudomonate

Aqueous precipitate obtained as in Example 2A containing 25 g mupirocin is added 50% aqueous methanol to a volume of 250 ml. Calcium oxide (1.8 g) is added to give a neutral solution (pH 7). The solution is evaporated in order to remove methanol. The methanol-free residue (120 ml) is diluted with water (50 ml) and allows crystallizing with stirring in room temperature. After 24 hours the mixture is filtered and the collected product is washed by slurrying with water (50 ml). The crystalline product is dried in a vacuum oven (50 mbar, 40° C.).

Comparison

Quality of process and final product:

|  | U.S. Pat. No. 4,222,942 Ex1 | U.S. Pat. No. 4,222,942 Ex2 | Invention Ex. 6a |
| --- | --- | --- | --- |
| Purity (final product) | 92-93% |  | 96% |
| Yield (from filtrate to final product) | 31% | 47% | 47% |
| Solvent use Liter/g product | 2.5 | 1.7 | 0.03 |
| "Steps" | 8 | 9 | 3 |

"Steps" = number of steps required to obtain a concentrated solvent extract from a clarified broth/filtrate

The invention claimed is:

1. A method for purifying mupirocin, consisting essentially of:
   a) precipitating mupirocin from an aqueous solution of mupirocin by adding an acid, wherein the pH of the aqueous solution during precipitation is in the range of 2.0 to 6.0; and
   b) recovering a mupirocin precipitate from the aqueous solution.

2. A method according to claim 1, wherein the acid is selected from the group consisting of acetic acid; citric acid; sulfuric acid; and hydrochloric acid.

3. A method according to claim 1, wherein the aqueous solution of mupirocin is a clarified fermentation broth.

4. A method according to claim 1, wherein the mupirocin precipitate is recovered in step b) by centrifugation or filtration.

5. The method according to claim 1, further comprising one or more additional steps selected from the group consisting of: a decolourisation step; a step for removal of hydrophilic components; a concentration step; an evaporation step; a clarification step; a water removal step; a drying step; a filtration step; an extraction step; and a crystallization step.

6. The method according to claim 3, wherein the fermentation broth is a filtered broth.

7. The method according to claim 1, wherein the pH is in the range of 3.5 to 5.

8. The method according to claim 1, wherein the pH is in the range of 4.2 to 4.6.

9. The method according to claim 1, further comprising c) dissolving the mupirocin precipitate in an organic solvent.

10. A method according to claim 9, wherein, in step c), the organic solvent is a polar, water immiscible or moderately soluble organic solvent.

11. A method according to claim 10, wherein the organic solvent is a ketone; an ester; an alkanol ; or a mixture comprising any combination of the foregoing solvents.

12. A method according to claim 10, wherein the organic solvent is pure methyl isobutyl ketone.

13. The method according to claim 11, wherein the organic solvent is methyl isobutyl ketone, ethyl acetate, n-butanol, or a combination thereof.

14. The method according to claim 9, further comprising d) recovering mupirocin from the organic solvent.

15. A method according to claim 14, wherein mupirocin is recovered from the solvent by crystallization, optionally after water removal from the solvent.

* * * * *